United States Patent [19]

Durant et al.

[11] 4,067,984
[45] Jan. 10, 1978

[54] PYRIDYLBUTYLAMINO ETHYLENE COMPOUNDS

[75] Inventors: Graham John Durant, Welwyn Garden City; John Colin Emmett, Codicote; Charon Robin Ganellin, Welwyn Garden City; Hunter Douglas Prain, Welwyn, all of England

[73] Assignee: Smith Kline & French Laboratories Limited, Welwyn Garden City, England

[21] Appl. No.: 729,567

[22] Filed: Oct. 4, 1976

Related U.S. Application Data

[60] Division of Ser. No. 629,193, Nov. 5, 1975, Pat. No. 4,002,759, which is a continuation-in-part of Ser. No. 468,617, May 9, 1974, Pat. No. 3,953,460.

[51] Int. Cl.$^2$ .................... A61K 31/395; C07D 213/84
[52] U.S. Cl. .............................. 424/263; 260/294.8 F; 260/294.8 G; 260/294.9; 260/296 R
[58] Field of Search ................. 260/294.8 G, 294.8 F, 260/294.9, 296 R; 424/263

[56] References Cited

U.S. PATENT DOCUMENTS

| | | | |
|---|---|---|---|
| 3,734,924 | 5/1973 | Black et al. | 260/309 |
| 3,736,331 | 5/1973 | Black et al. | 260/309 |
| 3,808,336 | 4/1974 | Durant et al. | 260/309 |
| 3,876,647 | 4/1975 | Durant et al. | 260/294.8 G |
| 3,905,984 | 9/1975 | Durant et al. | 260/294.8 H |
| 3,920,822 | 11/1975 | Durant et al. | 424/263 |

*Primary Examiner*—Alan L. Rotman
*Attorney, Agent, or Firm*—Joan S. Keps; Richard D. Foggio; William H. Edgerton

[57] ABSTRACT

The compounds are ethylene derivatives which are inhibitors of histamine activity, in particular, inhibitors of H-2 histamine receptors. A compound of this invention is 1-nitro-2-methylamino-2-[4-(3-chloro-2-pyridyl)-butylamino]ethylene.

7 Claims, No Drawings

PYRIDYLBUTYLAMINO ETHYLENE COMPOUNDS

This is a division of application Ser. No. 629,193 filed Nov. 5, 1975, now U.S. Pat. No. 4,002,759, which is a continuation-in-part of Ser. No. 468,617 filed May 9, 1974 now U.S. Pat. No. 3,953,460.

This invention relates to ethylene derivatives, in particular to pharmacologically active 1,1-diaminoethylene derivatives. These compounds are inhibitors of H-2 histamine receptors. In addition, this invention relates to pharmaceutical compositions comprising these compounds and to methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has been described by Black et. al. (Nature 1972, 236, 385) which are distinguished by the fact that they act at histamine receptors other than the H-1 receptor and these other receptors have been designated as H-2 receptors. This latter group of substances, to certain of which the present invention relates, are thus of utility in inhibiting certain actions of histamine which are not inhibited by the above-mentioned "antihistamines", that is they are H-2 histamine receptor inhibitors. Inhibitors of H-2 histamine receptors are useful, for example, as inhibitors of gastric acid secretion. The substances of this invention may also be of utility as inhibitors of certain actions of gastrin. In the treatment of certain conditions, for example inflammation, and in inhibiting the actions of histamine on blood pressure, a combination of H-1 and H-2 receptor inhibitors is useful.

The 1,1-diaminoethylene derivatives with which the present invention is concerned may be represented by the following general formula:

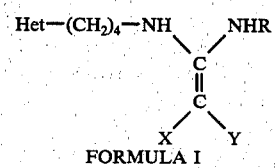

FORMULA I wherein X and Y, which may be the same or different, are hydrogen, nitro, cyano or SO$_2$Ar but are not both hydrogen; Het is a pyridine ring which ring is optionally substituted by lower alkyl, hydroxyl, halogen or amino; R is hydrogen, lower alkyl such as methyl or Het(CH$_2$)$_m$Z(CH$_2$)$_n$; Z is sulphur or methylene; $m$ is 0, 1 or 2 and $n$ is 2 or 3 provided that the sum of $m$ and $n$ is 3 or 4; and Ar is an aryl group such as phenyl optionally substituted by halogen or methyl, or a pharmaceutically acceptable acid addition salt thereof.

Throughout the present specification, by the term "lower alkyl" we mean an alkyl group containing from 1 to 4 carbon atoms.

It will be understood that the structure illustrated in Formula I and Formula I(a) below, is only one of several representations and that other tautomeric forms as shown in Formulae II and III and the other geometrical isomer shown in Formula IV are also covered by the present invention. In Formulae II to IV and I(a) R$^1$ represents Het-(CH$_2$)$_4$.

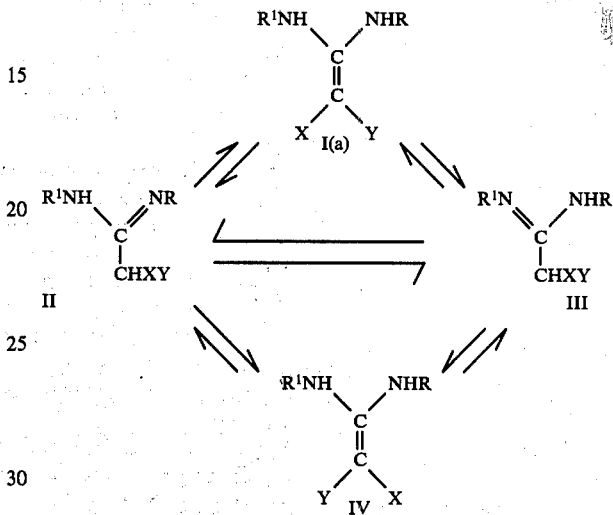

In a preferred group of compounds of Formula I, R is methyl or HetCH$_2$SCH$_2$CH$_2$. Most suitably, Het is pyridine optionally substituted by methyl, hydroxy, chloro, bromo or amino. It is also preferred that X should be nitro or cyano and Y should be hydrogen.

Particularly useful compounds are:
1-nitro-2-methylamino-2-[4-(3-chloro-2-pyridyl)-butylamino]ethylene,
1-nitro-2-methylamino-2-[4-(3-bromo-2-pyridyl)-butylamino]ethylene and
1-nitro-2-[4-(3-chloro-2-pyridyl)butylamino]-2-[2-((3-chloro-2-pyridyl)methylthio)ethylamino]ethylene.

A general method for the preparation of the compounds of the present invention is shown in the following Scheme 1:

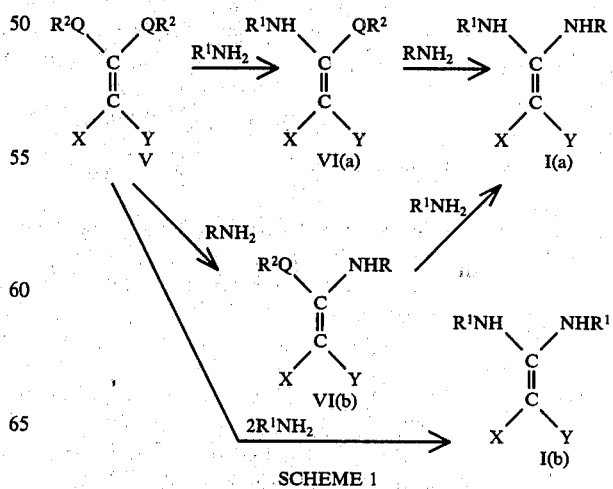

SCHEME 1

The starting material is a compound of Formula V wherein Q is sulphur or oxygen, preferably sulphur, and $R^2$ is lower alkyl such as methyl, or aralkyl, such as benzyl, but is preferably methyl. This may be reacted with one equivalent of $R^1NH_2$ or of $RNH_2$, $R^1$ and R having the same significance as in Formula I, to give respectively the compounds of Formulae VI(a) or VI(b) and then reacted with $RNH_2$ or $R^1NH_2$ respectively to give the compound of Formula I(a). In the case wherein R is the same as $R^1$ the reaction may be carried out in a single step by reacting the compound of Formula V with two equivalents of $R^1NH_2$ to give the product of Formula I(b). The reactions described in Scheme 1 may be carried out in a suitable solvent or in the absence of a solvent at a moderately elevated temperature, for example at from 90°–150° C.

The intermediate of Formula V wherein Q is sulphur (see Formula V(a) in the following Scheme 2:)

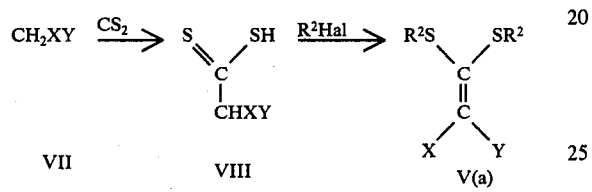

SCHEME 2 may be formed from the substituted methane of Formula VII by treatment of the latter with a strong base such as sodium hydride or sodium hydroxide and reaction with carbon disulphide to give the compound of formula VIII. Treatment of this substance with an alkyl or aralkyl halide of formula $R^2$Hal gives the required compound of Formula V(a).

An alternative method for the preparation of the compounds of Formula I(a) is shown in Scheme 3.

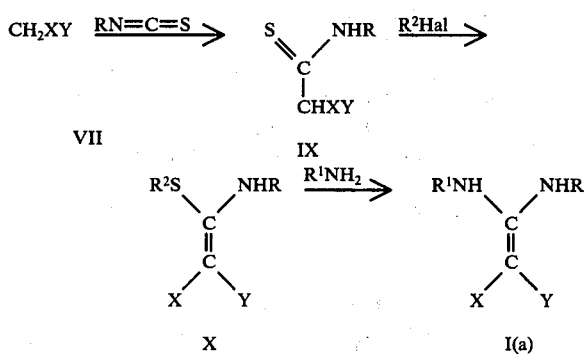

SCHEME 3

The substituted methane of Formula VII, after treatment with a strong base such as sodium hydride or sodium hydroxide, may be reacted with an isothiocyanate ester of Formula $RN=C=S$ wherein R is lower alkyl to give the compound of Formula IX and reaction of this with the alkyl or aralkyl halide of Formula $R^2$Hal results in the compound of Formula X wherein R is lower alkyl. Further reaction of the compound of Formula X with an amine of Formula $R^1NH_2$ yields the required compound of Formula I(a).

A further method which may be used in the preparation of compounds wherein R is hydrogen, X is $SO_2Ar$ and Y is hydrogen (Formula I(c)) is shown in Scheme 4:

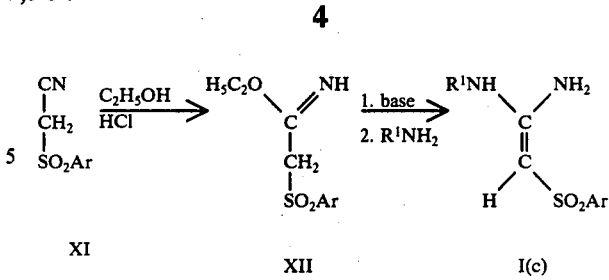

SCHEME 4

The arylsulphonylacetonitrile of Formula XI wherein Ar has the same significance as in Formula I is reacted under anhydrous conditions with ethanol and hydrogen chloride to give the iminoether of Formula XII. Treatment of this with a base and subsequent reaction with an amine of Formula $R^1NH_2$ gives the required product of Formula I(c).

It will be appreciated that the final stage of the reactions shown in Scheme 1, 3 and 4 may all be expressed by the following reaction:

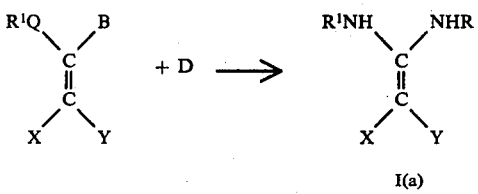

wherein B is RNH or $R^1NH$; D is $R^1NH_2$ or $RNH_2$; X, Y, R and $R^1$ have the same significance as in Formula I(a) and Q and $R^2$ have the same significance as in Formula V, provided that, when B is RNH, D must be $R^1NH_2$.

As stated above, the compounds represented by Formula I have been found to have pharmacological activity in the animal body as antagonists to certain actions of histamine which are not blocked by "antihistamines" such as mepyramine. For example they have been found to inhibit selectively the histamine-stimulated secretion of gastric acid from the perfused stomachs of rats anaesthetised with urethane at doses of from 0.5 to 256 micromoles per kilogram intravenously. Similarly, the action of these compounds is demonstrated by their antagonism to the effects of histamine on other tissues which, according to the above-mentioned paper of Black et. al., are H-2 receptors. Examples of such tissues are perfused isolated guinea pig atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 0.5 to 256 micromoles per kilogram, intravenously. Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol.

Pharmaceutical compositions comprising a pharmaceutical carrier and a compound of Formula I or a pharmaceutically acceptable acid addition salt thereof and methods of inhibiting H-2 histamine receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg to about 250 mg, most preferably from about 100 mg to about 200 mg.

The active ingredient will preferably be administered in equal doses one to three times per day. The daily dosage regimen will preferably be from about 150 mg to about 750 mg, most preferably from about 300 mg to about 600 mg.

Other pharmacologically active compounds may in certain cases be included in the composition. Advantageously the composition will be made up in a dosage unit form appropriate to the desired mode of administration, for example as a tablet, capsule or injectable solution. The invention is illustrated but in no way limited by the following Examples.

EXAMPLE 1

1-Nitro-2-methylamino-2-[4-(2-pyridyl)butylamino]-ethylene i. 2-(4-Aminobutyl)pyridine was reacted with 1-nitro-2,2-bis-methylthio-ethylene in pyridine at 60° for 3.5 hours. Concentration of the reaction mixture and crystallisation yielded 1-nitro-2-methylthio-2-[4-(2-pyridyl)-butylamino]ethylene, m.p. 78°.

ii. A mixture of 1-nitro-2-methylthio-2-[4-(2-pyridyl)-butylamino]ethylene and 33% ethanolic methylamine were heated on a steam bath for 15 minutes. Concentration, followed by crystallisation from ethyl acetate yielded the title compound m.p. 90°–91°.

(Found: C, 57.8; H, 7.2; N, 22.6%; $C_{12}H_{18}N_4O_2$ requires: C, 57.6; H, 7.2; N, 22.4%).

EXAMPLE 2

1-Nitro-2-methylamino-2-[4-(3-amino-2-pyridyl)-butylamino]-ethylene.

i.

Reaction of 2-chloro-3-nitropyridine in tetrahydrofuran with 2-(3-cyanopropyl)malonic acid diethyl ester in the presence of sodium hydride yields 1-(3-nitro-2-pyridyl)-1,1-bis-carboethoxy butyronitrile which on alkaline hydrolysis followed by treatment with mineral acid yields 2-(3-cyanopropyl)-3-nitropyridine. Reduction of this compound with diborane yields 2-(4-aminobutyl)-3-nitropyridine. Catalytic hydrogenation of the latter compound results in the formation of 3-amino-2-(4-aminobutyl)pyridine.

ii.

When 3-amino-2-(4-aminobutyl)pyridine is used as the starting material in the procedure of Example 1(i) and (ii), the title compound is produced.

EXAMPLE 3 i. a. Reaction of 3-amino-2-(4-aminobutyl)pyridine with sodium nitrite/hydrochloric acid and treatment of the resultant diazonium salt with cuprous chloride yields 3-chloro-2-(4-aminobutyl)pyridine. By a similar procedure employing cuprous bromide and hydrobromic acid 3-bromo-2-(4-aminobutyl)-pyridine may be produced and when the diazonium salt is treated with sulphuric acid the product is 3-hydroxy-2-(4-aminobutyl) pyridine.

i. b. Reaction of 3-nitro-2-(4-aminobutyl)pyridine with acetic anhydride/glacial acetic acid gives the corresponding acetylamino compound which is hydrogenated over palladium charcoal to yield 3-amino-2-(4-acetylaminobutyl)pyridine. Diazotisation of the latter compound and treatment of the product with cuprous chloride yields 3-chloro-2-(4-acetylaminobutyl)pyridine which, on hydrolytic removal of the acetyl protecting group gives 3-chloro-2-((4-aminobutyl)-pyridine.

When the corresponding series of reactions is carried out in which the diazonium salt obtained from 3-amino-2-(4-acetylaminobutyl)pyridine is reacted with cuprous bromide instead of cuprous chloride to give 3-bromo-2-(4-acetyl-aminobutyl) pyridine and hydrolysed the product is 3-bromo-2-(4-aminobutyl)pyridine. Similarly treatment of the diazonium salt with sulphuric acid gives 3-hydroxy-2-(4-acetylaminobutyl) pyridine, which on hydrolysis yields 3-hydroxy-2-(4-aminobutyl)pyridine.

ii. When
3-chloro-2-(4-aminobutyl)pyridine,
3-bromo-2-(4-aminobutyl)pyridine and
3-hydroxy-2-(4-aminobutyl)pyridine
are used as the starting materials in the procedure of Example 1(i) and (ii), the following compounds are produced:
1-nitro-2-methylamino-2-[4-(3-chloro-2-pyridyl)-butylamino]-ethylene,
1-nitro-2methylamino-2-[4-(3-bromo-2-pyridyl)-butylamino]-ethylene and
1-nitro-2-methylamino-2-[4-(3-hydroxy-2-pyridyl)-butylamino]-ethylene.

EXAMPLE 4

When, in the procedure of Example 3(ii), 1-nitro-2-methylthio-2-(4-(3-chloro-2-pyridyl)butylamino]ethylene, which is formed from the reaction of 3-chloro-2-(4-aminobutyl)pyridine with 1-nitro-2,2-bis-methylthioethylene, is reacted with ammonia or ethylamine instead of with methylamine the products are, respectively:
1-nitro-2-amino-2-[4-(3-chloro-2-pyridyl)butylamino]-ethylene and.
1-nitro-2-ethylamino-2-[4-(3-chloro-2-pyridyl)-butylamino]-ethylene.

EXAMPLE 5

Reaction of 1-nitro-2-methylthio-2-[4-(3-chloro-2-pyridyl)-butylamino]ethylene with the following amines:
3-chloro-2-(4-aminobutyl)pyridine,
3-chloro-2-[(2-aminoethyl)thiomethyl]pyridine,
3bromo-2-[(2-aminoethyl)thiomethyl]pyridine,
3-hydroxy-2-[(2-aminoethyl)thiomethyl]pyridine,
5-hydroxy-2-[(2-aminoethyl)thiomethyl]pyridine,
3-methyl-2-[(2-aminoethyl)thiomethyl]pyridine,
6-methyl-2-[(2-aminoethyl)thiomethyl]pyridine,
3-[(2-aminoethyl)thiomethyl]pyridine,
4-[(2-aminoethyl)thiomethyl]pyridine,
3-amino-2-[(2-aminoethyl)thiomethyl]pyridine,
2-(3-aminopropyl)thiopyridine and
2-[2-(2aminoethyl)thioethyl]pyridine,
results in the production of the following compounds, respectively:
1-nitro-2,2-bis-[4-(3-chloro-2-pyridyl)butylamino]ethylene,
1-nitro-2-[4-(3-chloro-2-pyridyl)butylamino]-2-[2-((3-chloro-2-pyridyl)methylthio)ethylamino]ethylene,
1-nitro-2-[4-(3-chloro-2-pyridyl)butylamino]-2-[2-((3-bromo-2pyridyl)methylthio)ethylamino]ethylene,
1-nitro-2-[4-(3-chloro-2-pyridyl)butylamino]-2-[2-((3-hydroxy-2pyridyl)methylthio)ethylamino]ethylene,
1-nitro-2-[4-(3-chloro-2-pyridyl)butylamino]-2-[2-((5-hydroxy-2-pyridyl)methylthio)ethylamino]ethylene,
1nitro-2-[4-(3-chloro-2-pyridyl)butylamino]-2-[2-((3-methyl-2-pyridyl)methylthio)ethylamino]ethylene,
1-nitro-2-[4-(3-chloro-2-pyridyl)butylamino]-2-[2((6-methyl-2-pyridyl)methylthio)ethylamino]ethylene,
1-nitro-2-[4-(3-chloro-2-pyridyl)butylamino]-2-[2-((3-pyridyl)methylthio)ethylamino]ethylene,
1-nitro-2-[4-(3-chloro-2-pyridyl)butylamino]-2-[2-((4-pyridyl)methylthio)ethylamino]ethylene,
1-nitro-2-[4-(3-chloro-2-pyridyl)butylamino]-2-[2-((3-amino-2-pyridyl)methylthio)ethylamino]ethylene,
1-nitro-2-[4-(3-chloro-2-pyridyl)butylamino]-2-[3-(2-pyridylthio)propylamino]ethylene and
1-nitro-2-[4-(3-chloro-2-pyridyl)butylamino]-2-[2-(2-pyridyl)ethylamino]ethylene.

EXAMPLE 6

1,1-Dicyano-2-methylamino-2-[4-(3-chloro-2-pyridyl)-butylamino]ethylene i. Sodium hydride (50% oil dispersion, 9.6g) was added portionwise to a solution of malononitrile (13.21 g) in dry dimethylformamide (150 ml). The mixture was stirred at 0° for 10 minutes and then to it was added dropwise a solution of methyl isothiocyanate (14.62 g) in dimethylformamide, maintaining the reaction temperature below 40°. The dark red solution was stirred for 45 minutes and a solution of methyl iodide (28.4 g) in dimethylformamide (25 ml) was then added. The reaction mixture was stirred vigorously for 20 minutes and then poured on to crushed ice (500 ml). The crude product (26 g, m.p. 115°) was filtered off and taken up in hot ethanol-ether (3:1, 600 ml). Filtration and cooling furnished 1,1-dicyano-2-methylthio-2-methylaminoethylene m.p. 119°–120°. Further recrystallisation from water gave a sample of m.p. 120°–121°.

(Found: C, 46.7; H, 4.6; N, 27.1; S, 20.8; $C_6H_7N_3S$ requires: C, 47.0; H, 4.4; N, 27.4; S, 20.9:)

ii. Reaction of 3-chloro-2-(4-aminobutyl)pyridine with 1,1-dicyano-2-methylthio-2-methylaminoethylene in acetonitrile at room temperature for one hour yields the title product.

EXAMPLE 7

1-Cyano-2-methylamino-2-[4-(3-chloro-2-pyridyl)-butylamino]-ethylene

3-Chloro-2-(4-aminobutyl)pyridine is added to a solution of 1-cyano-2-ethoxy-2-methylaminoethylene and stirred at 100° for 5 hours. Chromatographic purification of the reaction mixture yields the title compound.

EXAMPLE 8

Phenylsulphonyl acetonitrile (14.5 g) is suspended in anhydrous ether (100 ml) containing absolute ethanol (3.0 g) and into the stirred suspension is passed hydrogen chloride with stirring to a weight gain of 6.0 grams. Stirring is continued in the cold for 24 hours and the reaction mixture is then set aside in the cold for 3 days. The crystalline iminoether hydrochloride (13.4g) m.p. 148°–149° is collected. A solution of this hydrochloride (6.82 g) in aqueous potassium carbonate is extracted with ether and the ether extracts dried and concentrated to give the imino ether as the free base. This is dissolved in acetonitrile (50 ml) containing 3-chloro-2-(4-aminobutyl)pyridine (5.1 g) and the solution left at room temperature for 24 hours, heated at 50° for 5 hours and finally heated at reflux for 1 hour. The product is chromatographed on a column of neutral alumina and 1-benzenesulphonyl-2-[4-(3-chloro-2-pyridyl)butylamino]-ethylene isolated.

When the above procedure is repeated using as starting material the following acetonitriles:
(4-chlorophenyl)sulphonylacetonitrile,
(3,4-dichlorophenyl)sulphonylacetonitrile and
(4-methylphenyl)sulphonylacetonitrile
the following products are produced, respectively:
1-(4-chlorobenzene)sulphonyl-2-[4-(3-chloro-2-pyridyl)butylamino]ethylene,
1-(3,4-dichlorobenzene)sulphonyl-2-[4-(3-chloro-2-pyridyl)butylamino]ethylene and
1-(4-methylbenzene)sulphonyl-2-[4-(3-chloro-2-pyridyl)butylamino]ethylene.

EXAMPLE 9

By using diphenylsulphonylmethane as the starting material in place of malononitrile in the procedure of Example 6(i) there is produced 1,1-diphenylsulphonyl-2-methylthio-2-methylaminoethylene abd when this is reacted with 3-chloro-2-(4-aminobutyl)pyridine according to the procedure of Example 6(ii), the resultant product is 1,1-diphenylsulphonyl-2-methylamino-2-[4-(3 -chloro-2-pyridyl)butylamino]ethylene.

By the same procedure, starting from:
nitroacetonitrile,
phenylsulphonylnitromethane and
phenylsulphonylacetonitrile the following products may be produced:
1-cyano-1-nitro-2-methylamino-2[4-(3-chloro-2-pyridyl)-butylamino]ethylene,
1-nitro-1-benzenesulphonyl-2-methylamino-2-[4-(3-chloro-2-pyridyl)butylamino]ethylene and
1-cyano-1-benzenesulphonyl-2-methylamino-2-[4-(3-chloro-2-pyridyl)butylamino]ethylene.

EXAMPLE 10

When a solution of 1-nitro-2-methylamino-2-[4-(3-chloro-2-pyridyl)butylamino]ethylene in acetone is treated with ion-exchange resin IRA 400 in the chloride form, the corresponding hydrochloride addition salt is formed.

Similarly, by using the above procedure with ion-exchange resin IRA 400 which has been converted to the bromide, iodide and sulphate form respectively, the hydrobromide, hydriodide and hydrogen sulphate addition salts of 1-nitro-2-methylamino-2-[4-(3-chloro-2-pyridyl)butylamino]ethylene may be produced.

EXAMPLE 11

| Ingredients | Amounts |
| --- | --- |
| 1-Nitro-2-methylamino-2-[4-(3-chloro-2-pyridyl)butylamino]ethylene | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 12

| Ingredients | Amounts |
| --- | --- |
| 1-Nitro-2-methylamino-2-[4-(3-chloro-2-pyridyl)butylamino]ethylene | 200 mg |
| Lactose | 100 mg |

The ingredients are screened, mixed and filled into a hard gelatin capsule.

We claim:
1. A compound of the formula:

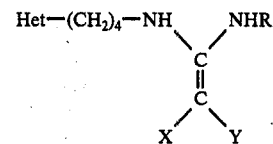

wherein X and Y, which may be the same or different, are hydrogen, nitro, cyano or $SO_2Ar$ but are not both hydrogen; Het is a pyridine ring which ring is unsubstituted or substituted by lower alkyl, hydroxyl, halogen or amino; R is $Het(CH_2)_mZ(CH_2)_n$; Z is sulphur or methylene; $m$ is 0, 1 or 2 and $n$ is 2 or 3 provided that the sum of $m$ and $n$ is 3 or 4, and Ar is phenyl which is unsubstituted or substituted by halogen, methyl or amino, or a pharmaceutically acceptable acid addition salt thereof.

2. A compound of claim 1 wherein R is Het $CH_2S—CH_2CH_2$.

3. A compound of claim 1 wherein Het is 2-pyridine substituted in the 3 position by chloro, bromo, hydroxy or amino.

4. A compound of claim 1 wherein X is nitro and Y is hydrogen.

5. A compound of claim 1 said compound being 1-nitro-2-[4-(3-chloro-2-pyridyl)butylamino]-2-[2-((3-chloro-2-pyridyl)methylthio)ethylamino]ethylene.

6. A pharmaceutical composition to inhibit H-2 histamine receptors comprising a pharmaceutical carrier and, in an effective amount to inhibit said receptors, a compound of claim 1.

7. A method of inhibiting H-2 histamine receptors which comprises administering orally or parenterally to an animal in need thereof, in an effective amount to inhibit said receptors, a compound of claim 1.

* * * * *

UNITED STATES PATENT AND TRADEMARK OFFICE
CERTIFICATE OF CORRECTION

PATENT NO. : 4,067,984

DATED : January 10, 1978

INVENTOR(S) : Graham John Durant, John Colin Emmett, Charon Robin Ganellin and Hunter Douglas Prain It is certified that error appears in the above-identified patent and that said Letters Patent are hereby corrected as shown below:

Column 4, lines 23-28, that portion of the left-hand formula reading $R^1Q\diagdown$ should read $R^2Q\diagdown$ Signed and Sealed this Twenty-third Day of May 1978

[SEAL]

Attest:

RUTH C. MASON
Attesting Officer

LUTRELLE F. PARKER
Acting Commissioner of Patents and Trademarks